US008227448B2

(12) United States Patent
Van Laere et al.

(10) Patent No.: US 8,227,448 B2
(45) Date of Patent: Jul. 24, 2012

(54) NUTRITIONAL COMPOSITION WITH HEALTH PROMOTING ACTION CONTAINING OLIGOSACCHARIDES

(75) Inventors: Katrien Maria Jozefa Van Laere, Heteren (NL); Elmo Wissing, De Bilt (NL)

(73) Assignee: N.V. Nutricia, Zoetermeer (NL)

( * ) Notice: Subject to any disclaimer, the term of this patent is extended or adjusted under 35 U.S.C. 154(b) by 672 days.

(21) Appl. No.: 10/451,881

(22) PCT Filed: Dec. 24, 2001

(86) PCT No.: PCT/NL01/00940
§ 371 (c)(1),
(2), (4) Date: Dec. 5, 2003

(87) PCT Pub. No.: WO02/051264
PCT Pub. Date: Jul. 4, 2002

(65) Prior Publication Data
US 2004/0071824 A1    Apr. 15, 2004

(30) Foreign Application Priority Data
Dec. 27, 2000 (EP) .................................. 00204776

(51) Int. Cl.
A61K 31/715 (2006.01)
(52) U.S. Cl. ........................... 514/54; 514/53
(58) Field of Classification Search ............ 514/54, 514/53
See application file for complete search history.

(56) References Cited

U.S. PATENT DOCUMENTS

| | | | | |
|---|---|---|---|---|
| 4,228,198 A * | 10/1980 | Burge et al. | ............... | 426/548 |
| 4,251,550 A * | 2/1981 | Proctor | .................... | 426/72 |
| 5,073,387 A | 12/1991 | Whistler | | |
| 5,230,918 A * | 7/1993 | Anderson et al. | ............ | 426/572 |
| 5,545,411 A * | 8/1996 | Chancellor | .................. | 424/439 |
| 5,906,852 A * | 5/1999 | Klemann et al. | ............. | 426/496 |
| 6,004,610 A | 12/1999 | Wang et al. | | |
| 6,241,983 B1 * | 6/2001 | Paul et al. | ................... | 424/93.4 |
| 6,548,662 B1 * | 4/2003 | Ohsaki et al. | ................ | 536/128 |
| 2007/0248649 A1 | 10/2007 | Sawatzki et al. | | |

FOREIGN PATENT DOCUMENTS

| | | |
|---|---|---|
| CA | 2340103 A1 * | 2/2000 |
| DE | 198 36 339 | 2/2000 |
| GB | 1072029 | 6/1967 |
| JP | 4-187093 | 7/1992 |
| JP | 04309501 A * | 11/1992 |
| JP | 5-304950 | 11/1993 |
| JP | 6-217761 | 8/1994 |
| JP | 09299093 A * | 11/1997 |
| JP | 11-346708 | 12/1999 |
| WO | WO 95/05182 | 2/1995 |
| WO | WO 99/61036 | 12/1999 |
| WO | WO 00/08948 | 2/2000 |
| WO | 00/33854 | 6/2000 |
| WO | WO 01/41581 A1 * | 6/2001 |

OTHER PUBLICATIONS

Vázquez et al., "Xylooligo-saccharides: manufacture and applications", Trends in Food Science & Technology, Departamento de Enxeneria Quimica, Universidade de Vigo (Campus Ourense), Edificio Politecnico, As Lagoas, 32004 Ourense, Spain, vol. 11 (2000) pp. 387-393.

Van Den Heuvel et al. "Nondigestible oligosaccharides do not interfere with calcium and nonheme-iron adsorption in young, health men", American Society for Clinical Nutrition, 1998: vol. 67—445-451.

Van Laere et al., "Fermentation of plant cell wall derived polysaccharides and their corresponding oligosaccharides by intestinal bacteria", Department of Food Technology and Nutricinal Sciences, Division of Food Science, Food Chemistry Group, Wagenmans Univesity and Research Centers, Booermeg 2, Netherlands, vol. 48, No. 5, 2000 pp. 1644-1652.

Yamada et al., "Structure and properties of oligosaccharides from wheat bran" Advances in cereal chemistry and technology in Japan, article based on presentation 1992 AACC annual meeting in Minneapolois, MN, Jul. 1993, vol. 38, No. 7 pp. 490-492.

* cited by examiner

Primary Examiner — Shaojia Anna Jiang
Assistant Examiner — Everett White
(74) Attorney, Agent, or Firm — Young & Thompson

(57) ABSTRACT

A nutritional composition having beneficial effect in the gastrointestinal tract, especially an anti-adhesion effect on pathogenic micro-organisms and a bifidogenic effect, contains non-digestible oligosaccharides, said oligosaccharides comprising, per daily dosage, 0.3-10 g of oligosaccharides containing at least one terminal arabinose unit. The nutritional composition may furthermore comprise 0.5-10 g of other non-digestible oligosaccharides selected from fructo-oligosaccharides, galacto-oligosaccharides, xylo-oligosaccharides and manno-oligosaccharides. The arabino-oligosaccharides can be obtained conveniently by controlled hydrolysis of arabinose-containing polysaccharides from natural (vegetable) origin.

3 Claims, No Drawings

NUTRITIONAL COMPOSITION WITH HEALTH PROMOTING ACTION CONTAINING OLIGOSACCHARIDES

The present invention relates to nutritional compositions with health-promoting action, in particular having a bifidogenic effect and having an anti-adhesive effect on pathogenic micro-organisms to the intestinal wall.

More specifically, in a first aspect, the invention relates to such a nutritional composition containing at least one oligosaccharide having at least one terminal arabinose unit.

As used herein, an oligosaccharide means a saccharide consisting of at least two, up to 20 glycosidically linked monosaccharide units, i.e. having a degree of polymerisation (DP) of 2-20. Saccharides of more than 20 units are referred to herein as polysaccharides. The oligosaccharides are poorly or non-digestible, i.e. are not readily converted to caloric substrates by the mammalian digestive enzymes.

The use of arabinose-containing polysaccharides in food products is known. GB 1,072,029 discloses the use of arabinogalactans having a molecular weight in the range of 70-95 kDa (DP 450-600) as a bulk sweetener combined with an artificial sweetener. According to U.S. Pat. No. 6,004,610, such arabinogalactans can be used together with hydrolysed guar gum as a dietary fibre in beverages, because of their low viscosity. WO 00/08948 (DE-198,36339) describes the use of a combination of an oligosaccharide (up to a hexasaccharide) and a polysaccharide (from a heptasaccharide upwards) for promoting flora of the human large intestine. Arabinans are mentioned as one of many possible polysaccharides.

The oligosaccharides to be used according to the invention have at least one terminal arabinose unit, i.e. at least one arabinose unit which is linked to the remainder of the oligosaccharide molecule by one (glycosidic) bond. These terminal arabinose units may be located at the end of the main chain of the oligosaccharide, whether it is a reducing end (having a free hemiacetal function) or a non-reducing end, or both, but they may also be located at the end of side chains to the main chain or be directly bound to the main chain by a single bond. In the present description, the oligosaccharides having one or more terminal arabinose units are also referred to as "arabino-oligosaccharides".

In its simplest form, an arabino-oligosaccharide of the invention is a dimer of two saccharide residues substituted, at least one of which is an L-arabinose residue. The other saccharide residue may be chosen from all saccharide residues, and in particular those saccharide residues that are present in naturally occurring saccharide polymers, such as galactose, arabinose, mannose and xylose. Most preferably the other saccharide is arabinose or galactose. Similarly, in trisaccharides, one or both of the terminal saccharide units are arabinose residue, while the remaining ones can be galactose, xylose, mannose etc., and the central arabinose can also be arabinose.

Longer arabino-oligosaccharides may be straight-chain (unbranched) or preferably branched oligosaccharides composed of any combination of saccharide units, as long as at least one terminal one is arabinose. The oligosaccharides may be linked by α-links, at 1,2-, 1,3-, 1,4- and/or (if applicable) 1,5- or 1,6- positions and, if ketoses are involved, 2,1-, 2,4-, 2,6- positions etc. L-Arabinose units in the arabino-oligosaccharides are usually in their furanoside form, but may also be in the pyranoside form. They are predominantly α-1,3- or α-1,5 linked. The number of L-arabinose residues present in the arabino-oligosaccharides may vary, provided that at least one arabinose residue, preferably at least two arabinose units, are present on at least one end of the oligosaccharide chain. Thus, only one (i.e. the at least one terminal residue), several or essentially all of the saccharide residues that form the backbone of the saccharide oligomer may be substituted with an L-arabinose residue. The backbone itself may consist of arabinose units or other units (galactoses, xyloses etc.).

The oligosaccharide units usually contain aldoses (and ketoses) only, but may also contain uronic acid, methylated or acylated or other commonly derivatised units.

The arabino-oligosaccharide may be a pure, exactly defined oligosaccharide or, more commonly a mixture of oligosaccharides with varying chain length and possibly also with varying branching patterns and/or varying saccharide composition. The arabino-oligosaccharides are preferably of natural origin, either directly isolated from their natural source, or isolated and hydrolysed or synthesised by chain lengthening. Hydrolysis may be effected chemically (acid) or enzymatically (glycanases) as described below, and synthesis is typically effected enzymatically (transferases).

Some suitable sources of such naturally occurring insoluble polymers include sugar beet extract, which contains mainly linear arabinans, cereal fibre, e.g. of wheat and barley, which contains branched arabino-xylo-saccharides (xylan chains which arabinose and other side units), and apple, potato and soybean fibre, which contain branched arabinogalactans of various types. They may also originate from arabinose-containing gums, such as gum arabic, tragacanth (the bassorin fraction thereof), gum ghatti etc.

The presence of one or more arabino-saccharides in a sample—such as the nutritional compositions of the invention and/or the hydrolysates mentioned below—can be assayed using analytical techniques known per se, such as high performance anion-exchange chromatography (HPAEC), and their amounts can be determined e.g. by preparative gel filtration followed by trifluoroacetic acid hydrolysis and HPAEC.

The nutritional composition of the invention may contain one or several different (types of) arabino-oligosaccharides. When the nutritional composition of the invention contains several different arabino-oligosaccharides, these may differ in their degree of polymerisation (DP, the total number of saccharide residues in the oligosaccharide chain); in the number and/or the position of the L-arabinose residues present on their oligosaccharide chain; in the (types of) the saccharide residues that form the oligosaccharide chain, the relative amounts thereof and/or the order thereof; and/or in any combination thereof. Also, the arabino-oligosaccharides present in the nutritional composition of the invention may differ in the manner in which they were obtained and/or in the starting material from which they were obtained, e.g. as further described below.

In the present invention, the arabino-oligosaccharides are preferably provided and incorporated into the nutritional composition in the form of a hydrolysate containing at least one arabino-oligosaccharide as defined above. Such hydrolysates form a further aspect of the invention. Preferably, such hydrolysates are obtained by hydrolysis of a starting material containing one or more L-arabinose-substituted polymers, preferably from natural origin. Of course, mixtures of such naturally occurring polymers and/or of such naturally available starting materials may also be used.

Generally, the hydrolysates of the invention will contain at least one oligomer, and usually several different oligomers, depending upon the starting material chosen, the way in which the starting material has been hydrolysed, as well as the further processing, separation and/or purification steps applied after hydrolysis (if any).

Furthermore, besides the desired arabinose-terminated oligomers, the hydrolysates of the invention may also contain amounts of arabinose monomers and other saccharide monomers. They may also contain amounts of arabinose-substituted saccharide polymers with a degree of polymerisation (chain length) of more than 20. Again, this will depend upon the starting material chosen, the way in which the starting material has been hydrolysed, as well as the further processing, separation and/or purification steps applied after the hydrolysis, if any.

According to the invention, it has been found that, in the nutritional compositions of the invention, the presence of certain amounts of monomers of polymers (including insoluble polymers) will not essentially influence (e.g. detract from) the health promoting action of the L-arabinose substituted oligomers of the invention, and also otherwise can be tolerated. However, preferably, the amount of oligomers in the hydrolysates used in the nutritional compositions of the invention is at least 5%, preferably at least 20%, based upon the total amount of oligomers, monomers and polymers (including insoluble polymers) present in the hydrolysates.

Thus, the hydrolysates that are incorporated into the nutritional compositions of the invention may contain, as far as arabinose-containing carbohydrates are concerned (weight ratios): 0-50% of monomers, 10-100% of oligomers (2- to 20-mers) and 0-70% of polymers (>20-mers). Preferably the ratios are 2-40% of monomers, 20-80% of arabinose-containing oligomers, 2-40% of other oligomers, and 10-60% of polymers. Most preferably, the ratios are 35-75% of arabinose-containing oligomers, 5-30% of other non-digestible oligomers, 5-30% of monomers, and 15-35% of non-digestible polymers.

The hydrolysis of the starting polymers—i.e. to provide the above hydrolysates—may be carried out in any manner known per se, depending upon the starting material used and the desired hydrolysate. Acid hydrolysis and enzymatic hydrolysis are preferred, with enzymatic hydrolysis being particularly preferred. Suitable conditions for acid hydrolysis include the use of aqueous media containing acids such as hydrochloric acid, sulphuric acid, phosphoric acid, an organic acid or polymeric or immobilised acids (acid resin) under usual conditions.

For enzymatic hydrolysis, any enzyme or enzyme combination suitable for degrading the starting polymers may be used. Preferably, these are endo-enzymes, and suitable examples and sources thereof will be clear to the skilled person. Enzymatic synthesis can be performed with transferase, i.e. enzymes capable of transferring an arabinose residue to a mono- or oligosaccharide.

Suitable conditions for enzymatic hydrolysis will depend upon the starting material and the enzyme used. Preferably, a pH and a temperature near the optimum pH and temperature of the enzyme is used. Suitable conditions may for instance comprise the use of purified endogalactanase of 1 μg/ml in an aqueous substrate solution at a pH between 4.5 and 6, at a temperature of about 30° C. for 30 minutes to 3 hours at a concentration of starting arabinogalactan of 0.5-20 wt. %. As will be clear to the skilled person, the starting materials, the enzymes used, the hydrolysis conditions and the optional further processing steps most preferably are chosen such that the resulting hydrolysate is still acceptable for use in the nutritional compositions of the invention. Usually, this will involve the use of starting materials, enzymes etc. acceptable for use in food applications, e.g. having the GRAS status.

Generally, the hydrolysis is allowed to proceed until the hydrolysate obtained contains at least 10%, preferably at least 20%, most preferably at least 50% arabinose-containing oligomers. The progress of the hydrolysis may be followed using any suitable method, which will usually involve determining the amount of the oligomers formed, the amount of monomers formed, and/or the amount of polymers remaining. Suitable techniques, such as chromatography techniques, will be clear to the skilled person. The arabinose-containing starting polymers may be used as such, or may be purified so as to increase the yield of desired product. Such pre-treatment may include chemical extraction (sodium hydroxide solution) or physical extraction (extrusion).

For instance, for the degradation of naturally occurring polymers mentioned below, and for the transfer synthesis, respectively, the following enzymes be used:

| Starting material | Enzyme | Oligomer |
|---|---|---|
| arabinan | endo-arabinase | arabino-oligosaccharides |
| arabinoxylan | endo-xylanase | arabinoxylo-oligosaccharides |
| arabinogalactan | endo-galactanase | arabinogalacto-oligosaccharides |
| arabinobiose | arabinofuranohydrolase | arabinotriose and higher homologues |

The hydrolysates obtained after the hydrolysis may be incorporated as such into the nutritional compositions of the invention, or after further processing/purification steps, for instance to quench the hydrolysis reaction (e.g. to inactivate the enzyme(s) and/or to increase the pH), to remove components of the hydrolysis mixture such as salts and/or the enzymes used; to remove byproducts of the hydrolysis reaction; and/or the reduce the amount of monomers or the amount of soluble or insoluble polymers. This may be carried out using any purification and/or processing techniques known per se, including neutralisation, precipitation, filtration, dialysis, ultrafiltration, or a suitable combination of such steps. These steps preferably result in a hydrolysate as described above for incorporation in the nutritional compositions of the invention.

Also, a nutritional composition of the invention may contain a combination of such hydrolysates, i.e. obtained from different starting materials, using different hydrolysis conditions (e.g. enzymes used and/or final degree of hydrolysis) and/or different further purification/processing steps.

Thus, in a further aspect, the invention relates to a method for preparing a hydrolysate containing at least one L-arabinose substituted oligosaccharide, said method comprising hydrolysing one or more L-arabinose substituted polymers and optionally one or more further processing steps known per se.

The invention is based on the discovery that the oligomeric arabans have a health-promoting action, in particular with respect to the prevention and/or treatment of disorders of the gastrointestinal tract. In particular, it has been found that the arabino-oligosaccharides can prevent and/or reduce adhesion or translocation of undesired micro-organisms to the intestinal wall, and also have a "bifidogenic" effect, by which is meant that they can promote a healthy flora in the gastrointestinal tract, which in infants makes it more similar to the flora of breast-fed infants and/or can be used to prevent and/or treat any disturbance in the naturally occurring flora in the gastrointestinal tract. These effects are especially beneficial in clinical patients and in newborns. Also, the products induce an enhanced immune function and an improved absorption of minerals like calcium and magnesium, which is beneficial to menopausal woman, elderly persons, and patients suffering from a disturbed intestinal function.

The compositions of the invention may provide their health-promoting action throughout the entire small and large intestine and/or one or more parts thereof, including the duodenum, jejunum, ileum and colon. Similarly, the compositions of the invention may also provide their anti-adhesion and/or their bifidogenic effect throughout the entire intestinal tract and/or parts thereof, which may be the same or different parts.

For this purpose, the nutritional compositions of the invention may contain several different oligomers, which may provide for health promoting action in different parts of the gastrointestinal tract. Also, the nutritional compositions of the invention may contain several different oligomers, one or more of which provide for an anti-adhesion effect and one or more of which provide for a bifidogenic effect. Also, nutritional compositions of the invention may contain different oligomers (e.g. with different degrees of hydrolysis) so as to provide for an anti-adhesion effect in different parts of the gastrointestinal tract, and/or several different oligomers (e.g. with different degrees of hydrolysis) as to provide for a bifidogenic effect in different parts of the gastrointestinal tract.

In this way, oral administration of a nutritional composition of the invention containing several different oligomers, suitably chosen, can produce the desired health-promoting action in several or in essentially all parts of the gastrointestinal tract simultaneously. Also, by oral administration of such a composition, both an anti-adhesion and a bifidogenic effect can be obtained simultaneously, in one, several or essentially all parts of the gastrointestinal tract, which may be the same of different. Also, by using a combination of several different oligomers, a synergistic effect may be obtained.

According to one preferred aspect, the nutritional compositions of the invention provide their anti-adhesion effect in the small intestine and/or provide their bifidogenic effect in the large intestine. Generally, for an anti-adhesion effect, small linear and branched oligomers, preferably with a degree of polymerisation (DP) of 2-10 are most suited. For a bifidogenic effect, oligomers which are branched and have a DP of up to 20 are most suited.

Generally, to obtain the health promoting action effect of the invention, the oligomers will usually be administered to an adult in an amount ranging between 0.01 and 0.5 g per kg body weight per day; and to an infant in an amount ranging between 0.02 and 1.0 g per kg body weight per day. These amounts of oligomers may be administered as a single dose per day or as several doses per day, with 1-6, in particular 1-3 doses per day being preferred.

More specifically, to obtain the anti-adhesion effect of the invention, the arabino-oligosaccharides will usually be administered to an adult in an amount ranging from 0.01 to 0.2 g per kg body weight per day; and to an infant in an amount ranging from 0.02 to 0.4 g per kg body weight per day; again as a single or as several doses per day.

To obtain the bifidogenic effect of the invention, the oligomers will usually be administered to an adult in an amount between 0.1 and 0.5 g per kg body weight per day; and to an infant in an amount between 0.2 and 1.0 g per kg body weight per day; also as a single or as several doses per day.

From the above, it will be clear that—as the amount of arabino-oligosaccharides that is usually administered to obtain the bifidogenic effect is larger than the amount usually administered to obtain the anti-adhesion effect—administering the arabino-oligosaccharides to obtain the bifidogenic effect will usually also result in a anti-adhesion effect, depending upon the oligomers present.

The administration of the nutritional compositions of the invention may be continued until the desired health promoting action is obtained and/or—when administered as prophylactics—until the individual is no longer exposed to conditions which require (additional) protection against disorders of the gastrointestinal tract.

The nutritional composition of the invention may be in any form suitable for human administration, and in particular suitable for administration to any part of the gastrointestinal tract. Usually, and preferably, this will involve (compositions suitable for) oral administration, although for instance administration into the gut—such as through a tube or catheter—also forms part of the invention.

In particular, the nutritional composition may be in the form of a food supplement or in the form of a complete food which is ready for consumption, such as a total food or infant formula.

When the composition of the invention is in the form of a food supplement, it can be in a form for separate administration, such as a capsule, a tablet, a powder, a sachet, a liquid composition (e.g. droplets) or a similar form, containing preferably a unit dose of oligomers of the invention. Such a supplement may further comprise one or more adjuvants, carriers or excipients suitable for use in food supplements, as well as one or more of the further components and/or additives described below.

The food supplement may also be in the form of a powder, a liquid composition (e.g. droplets) or a similar form, which is added to or mixed with a suitable food (composition) or a suitable liquid or solid carrier, for the preparation of a food or drink which is ready for consumption. For instance, the food supplement may be in the form of a powder which can be mixed with, and/or reconstituted with, water, milk, fruit juice, toddler drinks, oral rehydration solution (to provide a so-called ORS drink), etc. It can also be in the form of a powder or liquid that can be mixed with solid foods or with foods with a high-water-content, such as fermented foods, for example yoghurt.

A food supplement according to the invention preferably contains the non-digestible arabinose-containing oligosaccharides (1) together with non-digestible polysaccharides (3) (whether or not containing arabinose units), optionally other non-digestible oligosaccharides (2) and digestible carbohydrates (4), such as glucose, fructose, and/or malto-dextrins, in a weight ratio of (1)+(2)+(3) to (4) of 1:5 to 24:1. The amount of (1) is 1-90% of the total dry weight of the supplement, preferably 5-40%, the amount of (2) is 0-50%, preferably 2-25%, the amount of (3) is 2-50%, preferably 5-30%, and the amount of (4) is 4-80%, preferably 10-50%. The remainder, if any, may be vitamins, minerals, proteins, colorants, preservatives and the like.

The nutritional compositions of the invention can also be in the form of a solid, semi-solid or liquid food which is ready for consumption. Such a food will usually comprise—besides the one or more oligomers of the invention—a food or food base known per se, and can for instance be prepared by adding a food supplement as described above to a food or food base known per se;

adding one or more oligomers of the invention to a food or food base known per se; and/or incorporating one or more oligomers of the invention to a food or food base known per se during the preparation thereof.

As such, the nutritional compositions in the invention can be foods for oral consumption, for instance a total food or an infant formula. They can also be foods for administration by tube or catheter into the stomach, e.g. by tube or catheter.

The nutritional composition of the invention, whether in the form of a food for consumption or a food supplement, can further comprise all desired components and/or additives for use in foods or food supplements, including but not limited to flavours, colourings, preservatives, sugar, etc., as long as these do not interfere (too much) with the desired health promoting action of the oligomers. The composition can contain one or more peptides and/or proteins, lipids, carbohydrates, vitamins, minerals and trace elements, in usual amounts.

A complete food according to the invention preferably comprises proteins (4-35%, preferably 7-25%), lipids (4-40%, preferably 7-35%), digestible carbohydrates (30-90%, preferably 35-75%), in addition to 0.07-6%, preferably 0.2-4% of non-digestible arabinose-containing oligosaccharides. The balance up to 100% (all percentages by weight) may be other non-digestible carbohydrates, e.g. in a proportion of 0-10%, preferably 0.1-5%, at least half of which preferentially consists of oligosaccharides. Where the complete food is a tube-feeding, the amount of non-digestible arabinose-containing oligosaccharides is preferably 0.07-2.5%, in particular 0.2-2%. In an infant formula, the amount of non-digestible arabinose-containing oligosaccharides is preferably higher, i.e. 0.15-6%, in particular 0.4-4%.

The composition of the invention can also contain one or more additional substances that inhibit bacterial adhesion to the epithelial wall of the gastrointestinal tract, including mannans, galacturonic acid oligomers, preferably of natural origin, as a result of which a synergistic effect may be obtained.

The compositions can and preferably do also contain prebiotics, as well as prebiotic compounds, in particular fibres and proteins. Fibres in particular include soluble and insoluble non-digestible polysaccharides, such as non-starch polysaccharides (of the cellulose, hemicellulose and other types), resistant starch, gums etc. It is particularly preferred that the compositions of the invention comprise other non-digestible oligosaccharides, which are usually soluble. These include (trans-)galacto-oligosaccharides (TOS or GOS), fructo-oligosaccharides (FOS), xylo-oligosaccharides (XOS) and manno-oligosaccharides. These other oligosaccharides are preferably obtained from natural sources, either by direct extraction, e.g. in the case of inulin (FOS), or by hydrolysis of suitable polysaccharide or polysaccharide mixture, e.g. in the case of inulin and levan (FOS), galactans and galactomannans (TOS), and xylans and other hemicellulose constituents (XOS) or by enzymatic synthesis using the appropriate transferases, e.g. in the case of FOS and TOS.

These other oligosaccharides may be added as such, especially if they are obtained by direct extraction or synthesis (FOS or TOS) or they may be co-hydrolysed with the arabino-polysaccharides to obtain an oligosaccharide fraction containing both arabino-oligosaccharides of the invention and other oligosaccharides, e.g. xylo- and/or galacto-oligosaccharides. These may (further) help to maintain and/or restore the intestinal flora, which again may result in a synergistic effect. The amounts of other oligosaccharides may vary, e.g. from 10% to 400% with respect to the total amount of non-digestible oligosaccharides, especially in a ratio of arabino-oligosaccharides (AOS) to other oligosaccharides between 1:3 and 3:1.

The compositions may advantageously also contain probiotic organisms such as bifidobacteria, lactobacilli and other lactic acid bacteria, e.g. at levels of at least $10^7$ viable microorganisms per daily dose per individual.

The compositions of the invention may also contain antibodies such as immuno-globulins that act specifically against the pathogenic micro-organisms, more specifically against enterotoxigenic *E. coil* strains, rotaviusses, *Clostridia, Salmonella* and/or *Campylobacter* species. These immunoglobulins are used in amounts of at least 20 μg per 100 g of the composition. The compositions can also contain at least 2 mg/100 g of the composition sialylated compounds, and at least 2 mg/100 g product of a bactericidal compound, such as preferably lactoferrin.

Also, the compositions of the invention may contain other health-promoting components known per se, such as medicaments, etc. In particular, the compositions may contain compounds which have a beneficial influence on the gastrointestinal tract, such as glutamine/glutamate or precursors thereof, which provide fuel for the cells of the gastrointestinal wall. Again, by the use of such a combination, a synergistic effect may be obtained.

The amount of the one or more oligomers described above that is present in a nutritional composition of the invention will usually depend upon—inter alia—the oligomers used, the form of the composition (e.g. as a total food or as a food supplement), the intended health promoting effect (e.g. adhesion inhibiting and/or bifidogenic), and the number of doses per day to be administered. Generally, the amount will be such that it allows easy administration of the oligomers in the daily amounts mentioned above, e.g. as a single dose or as several doses per day.

Amounts to be administered are given below with reference to a daily dosage, unless indicated otherwise. A daily dosage for an adult is taken as corresponding to an energy intake of 2000 kcal/day, or about 25 kcal per kg body weight per day. Thus, an amount given as a daily dosage, where complete foods are concerned, means an amount per 2000 kcal energy for an adult. For an infant, the energy intake is usually higher e.g. about 50 kcal per kg body weight per day. For food supplements, the amount are naturally higher: if the supplement contains energy components, such as carbohydrates, the amount per daily dosage may be e.g. the amount per 200 or per 400 kcal energy. The amounts given may also refer to the total weight of the nutritional composition as given below and in the appending claims.

Usually, a nutritional composition of the invention will contain a unit dose of the oligomers and/or a predetermined amount of hydrolysate. For instance, a food supplement of the invention may contain a total of 0.3 to 10.0 g of arabinose-containing oligomers, and/or a total of 2.5 to 50 g of hydrolysate of the invention. Preferred amounts are between 0.5 and 8 g oligomers and between 5 and 25 g hydrolysate. A total food of the invention may for instance contain a total of 0.5 to 10.0 g of oligomers (preferred 1.0 to 8 g), and/or a total of 2.5 to 50 g (preferred 5 to 25 g) of hydrolysate of the invention. A infant formula of the invention may for instance contain a total of 0.5 to 10.0 g (preferred 1.0 to 8.0 g) of oligomers, and/or a total of 1 to 20 g (preferred 2.0 to 16.0 g) of the hydrolysate of the invention.

The nutritional compositions of the invention can be used to prevent or treat any of a number of disorders of the gastrointestinal tract, and/or reduce or alleviate the symptoms of such disorders. These disorders include, but not limited to infectious diarrhoea, traveller's diarrhoea, antibiotic-associated diarrhoea. The compositions of the invention are particularly suited for the prevention of infectious diarrhoea caused by micro-organisms such as *E. coli* or *Shigella*, as may occur during travel and/or after treatment with antibiotics.

For these and other applications, the oligomers provide the following effects and advantages:

they reduce and/or prevent of the adhesion of pathogens such as *E. coli* (HEC) and *Shigella* to the (wall of) the gastrointestinal tract, and in particular the intestinal wall; this reduces the risk of infection;

they promote the natural flora in the gastrointestinal tract and thereby reduce or prevent the growth of pathogens;

they promote and/or restore normal digestion and a proper electrolyte balance in the gastrointestinal tract.

In these and other applications, some further advantages of the use of the oligomers include:

they stimulate growth of species of bifidobacteria which are not stimulated by e.g. TOS, which is also considered as a prebiotic;

the fermentation of the oligomers of the invention may improve the absorption from calcium from the colon;

the oligomers have a viscosity which makes them particularly suited for the preparation of food for administration into the stomach by tube or catheter.

In a further aspect, the invention therefore relates to the use of at least one oligomer, and/or of an hydrolysate containing at least one oligomer as described above, in (the preparation of) a nutritional composition for the prevention and/or treatment of disorders of the gastrointestinal tract, such as disorders listed above, in particular for the prevention and/or treatment of diarrhoea, and in particular infectious diarrhoea.

The invention also relates to the use of at least one oligomer, and/or of an hydrolysate containing at least one oligomer as described above, in (the preparation of) a nutritional composition for reducing and/or preventing the adhesion and/or the growth of undesired micro-organisms such as pathogens to the (wall of) the gastrointestinal tract.

Also, in a further aspect, the invention also relates to the use of at least one oligomer, and/or of an hydrolysate containing at least one oligomer as described above, in (the preparation of) a nutritional composition for promoting or restoring the natural intestinal flora, and/or for preventing or reducing a disturbance of the natural intestinal flora.

Although the oligomers of the invention most preferably have a degree of polymerisation of 2-20, it should be clear that some health-promoting action may also be provided by oligomers of the general type, but with a somewhat larger degree of polymerisation, e.g. in the region of 21-30. Thus, although not preferred, the use of minor amounts of such oligomers, if it results in a health promoting action as described herein, should be considered equivalent to the embodiments described above.

EXAMPLES

Example 1

Production of Arabiizo-oligosacchiarides

Commercial sugar beet fibre (Atlantis series 2025) containing 80% dietary fibre, about half of which is soluble, contains about 39% arabinose (determined using HPAEC after TFA hydrolysis). The fibre is dissolved in acetate buffer (50 mM, pH 5) and is incubated at 40° C. with an endo-arabinase, e.g as present in commercial enzyme preparation Ultra SP (Novo Nordisk). After the incubation period, the reaction is stopped using a heating step (100° C.). The product is spray-dried and contains about 10% of monomer (largely arabinose), 20% of arabino-oligosaccharides (DP 2-6), 10% other oligosaccharides (DP 2-20), 10% soluble fibre (DP >20) and 50% insoluble fibre (DP>20).

Example 2

Production of Arabino-oligosaccharides

Arabinan (Megazyme, 50% arabinose in polymer form) was incubated with Ultra SP (10 µl) for 3 h at 40° C. and pH 5. After deactivation of the enzyme, the product was freeze-dried and analysed using HPAEC. After 3 h of incubation, the carbohydrate fraction consisted of about 25% of monomer, 40% of arabino-oligosaccharides (DP 2-20), 10% other oligosaccharides (containing no arabinoses) and 25% of material having a DP above 20. After filtration over a 0.1 mm filter, the sterile liquid is spray-dried.

Example 3

Anti-adhesive Effect

Different oligosaccharides obtained by hydrolysis of fibres were used to measure inhibition of pathogen binding to human colon cancer cells. Cells for the binding experiment are grown under standard conditions. The growth medium is removed from the cells and 0.2 ml of minimal essential medium, 0.4 ml EHEC solution ($2 \times 10^8$ cfu/ml) and 0.4 ml of test solution (5-10 mg/ml hydrolysed fibre) is added. Appropriate blanks are used as controls. Cells are incubated for an hour at 37° C., after which the medium is removed. The cells are washed five times with PBS buffer, lysed, homogenised, diluted and plated to count colony-forming units, following standard procedures. Comparison of the amount of cfu's found with the blank and with one of the fractions, the inhibiting power of the fraction can be calculated as percentage reduction in binding. The table below summarises results of binding reduction. The results show that arabinose-containing oligosaccharides reduce the binding of EHEC to Caco2 cells better than any of the other oligosaccharides. Especially arabino-oligosaccharides shows very high binding reduction capacity but also arabinoxylo- and arabinogalacto-oligosaccharides show more that 60% reduction in binding. All other oligosaccharides (non arabinose-containing) have lower than 60% binding reduction activity.

| oligosaccharide | % binding reduction |
| --- | --- |
| arabinan | 91 |
| arabinoxylan | 75 |
| arabinogalactan | 63 |
| galactan | 52 |
| xylan | 3 |
| galactomannan | 24 |
| galacturonan | 21 |
| lactose | 28 |

Example 4

Bifidogenic Effect

Hydrolysed arabans (DP 2-9, containing about 10% monomer) from sugar beet (see example 3) stimulate the growth of *Bifidobacterium* strains: *lactis, infantis, angulatum* and *pseudocatelulatum*.

When 150 mg of specific oligosaccharides is added to 5 g faeces, the growth of bifidobacteria increases. When the oligosaccharides are trans-galacto-oligosaccharides, the bifidobacteria content increases with 5%. When the oligosaccharides are arabino-galactans, the number increases by about 38% toe over the same time period. When arabinose oligomers are used, the increase is about 68%.

Example 5

Nutritional Composition

An infant formula is prepared by mixing the following components.

| Component | g per 100 ml |
|---|---|
| Protein equivalents | 1.40 |
| Casein | 0.60 |
| Whey protein | 0.80 |
| Carbohydrates | 7.0 |
| Lactose | 1.3 |
| Glucose | 0.2 |
| Maltose | 2.1 |
| Polysaccharides | 3.5 |
| Lipids | 3.6 |
| Saturated | 1.4 |
| Mono-unsaturated | 1.7 |
| Poly-unsaturated | 0.5 |
| Arabino-oligosaccharides according to example 1 | 0.1 |

Further components: minerals, trace elements and vitamins in amounts as recommended by the EEC regulation 321.

Example 6

Supplement for the Treatment of Diarrhoea

The product of example 2 (10 kg dry weight), glucose (20 kg), potassium citrate (2.9 kg) and sodium chloride (3.2 kg) are dissolved in water to a total of 1000 l in a tank to produce a liquid.

Example 7

Supplement for Enhancing Intestinal Function

A mixture of 2 g of hydrolysed arabinoxylans, 2 g of fructo-oligosaccharides, 2 g of soy polysaccharides, 1 g of a probiotic preparation containing about $10^{10}$ freeze-dried lacto-bacillus cells, 5 g maltodextrs and flavourings is prepared as a daily dosage form of 12 g packaged in sachets. It improves the intestinal function.

The invention claimed is:

1. A complete food composition containing proteins (4-35wt. %), lipids (4-35 wt. %), and digestible carbohydrates (30-90 wt. %), said composition containing, on a dry weight basis, 0.07-6% of arabinoxylo-oligosaccharides containing at least one L-arabinose unit at least one end of the oligosaccharide chain.

2. A complete food composition according to claim 1, which is a liquid tube-feed composition containing, on a dry weight basis, 0.07-2.5% of said arabinose-containing oligosaccharides.

3. A complete food composition according to claim 1, which is an infant formula containing, on a dry weight basis, 0.15-6% of said arabinose-containing oligosaccharides.

* * * * *